United States Patent
Haas et al.

(10) Patent No.: US 6,342,646 B1
(45) Date of Patent: Jan. 29, 2002

(54) CATALYTIC HYDROGENATION OF 3-HYDROXYPROPANAL TO 1,3-PROPANEDIOL

(75) Inventors: Thomas Haas, Frankfurt a.M.; Bernd Jaeger, Darmstadt; Willi Hofen, Rodenbach; Rudolf Vanheertum, Kahl, all of (DE)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/382,970

(22) Filed: Aug. 25, 1999

Related U.S. Application Data

(60) Provisional application No. 60/146,649, filed on Jul. 30, 1999.

(51) Int. Cl.⁷ .......................................... C07C 29/141
(52) U.S. Cl. ..................................................... 568/862
(58) Field of Search ........................................ 568/862

(56) References Cited

U.S. PATENT DOCUMENTS

| | | | |
|---|---|---|---|
| 2,434,110 A | * 1/1948 | Hatch et al. | 260/602 |
| 5,015,789 A | 5/1991 | Arntz et al. | 568/862 |
| 5,171,898 A | * 12/1992 | Arntz et al. | 568/862 |
| RE34,349 E | * 8/1993 | Unruh et al. | 568/862 |
| 5,276,201 A | 1/1994 | Haas et al. | 568/491 |
| 5,284,979 A | 2/1994 | Haas et al. | 568/491 |
| 5,334,778 A | * 8/1994 | Haas et al. | 568/862 |
| 5,364,984 A | 11/1994 | Arntz et al. | 568/862 |
| 5,364,987 A | 11/1994 | Haas et al. | 568/866 |
| 5,426,249 A | 6/1995 | Haas et al. | 568/862 |
| 5,962,745 A | 10/1999 | Brossmer et al. | 568/491 |
| 6,093,786 A | 7/2000 | Kelsey | 528/271 |

FOREIGN PATENT DOCUMENTS

| | | | |
|---|---|---|---|
| EP | 713 853 | 5/1996 | C07C/45/64 |
| WO | WO 98/23662 | 6/1998 | C08G/63/00 |
| WO | WO 00/10953 | 3/2000 | C07C/29/80 |
| WO | WO 00/14041 | 3/2000 | C07C/29/141 |

* cited by examiner

*Primary Examiner*—Peter O'Sullivan

(57) ABSTRACT

The present invention provides an improved process for the hydrogenation of 3-hydroxypropanal to 1,3-propanediol which comprises purifying an aqueous solution of 3-hydroxypropanal by contacting said aqueous solution with a purifying agent prior to hydrogenation.

16 Claims, No Drawings

CATALYTIC HYDROGENATION OF 3-HYDROXYPROPANAL TO 1,3-PROPANEDIOL

This application claims priority benefit of U.S. Provisional Application No. 60/146,649, filed Jul. 30, 1999.

FIELD OF THE INVENTION

This invention relates to an improved process for the production of 1,3-propanediol by catalytic hydrogenation of 3-hydroxypropanal (HPA).

TECHNICAL BACKGROUND 1,3-Propanediol is used as a monomer unit for polyesters and polyurethanes and as a starting material for synthesizing cyclic compounds.

Various processes are known for the production of 1,3-propanediol via 3-hydroxypropanal (HPA) which start either from C2 and C1 structural units or from a C3 structural unit, such as, for example, acrolein. When acrolein is used, it is first hydrated in aqueous phase in the presence of an acidic catalyst to form HPA. After removing the unreacted acrolein, the aqueous reaction mixture formed during hydration still contains, in addition to 85 wt % based on total organics of 3-hydroxypropanal, approximately 8 wt % 4-oxaheptane-1, 7-dial and further organic components in smaller proportions by weight. This reaction mixture is hydrogenated in the presence of hydrogenation catalysts to produce 1,3-propanediol. The 1,3-propanediol is recovered from the reaction mixture by distillation and/or extraction based methods known to those skilled in the art.

U.S. Pat. No. 5,334,778 discloses a two stage process for hydrogenating 3-hydroxypropanal which yields 1,3-propanediol having a residual carbonyl content, expressed as propanal, of below 500 ppm. The hydrogenation is carried out at 30° C. to 80° C. to a 3-hydroxypropanal conversion of 50 to 95% and then is continued at 100° C. to 180° C. to a 3-hydroxypropanal conversion of substantially 100%. Suitable hydrogenation catalysts therein include Raney nickel suspension catalysts, and supported catalysts based on platinum or ruthenium on activated carbon, Al2O3, SiO2, or TiO2 as well as nickel on oxide- or silicate-containing supports.

According to U.S. Pat. No. 5,015,789, very active nickel catalysts exhibit inadequate long-term stability, with a rapid drop in hydrogenation conversion and reaction speed upon repeated use of the catalyst. This results in frequent replacement of the entire catalyst packing, which is associated with known problems in the disposal and working up of compounds containing nickel. In addition, soluble nickel compounds can form in the process and are released into the product stream, requiring further steps to separate the resulting contaminants.

Copending patent application, Ser. No. 60/099,235 discloses a two-stage process for the production of 1,3-propanediol which comprises hydrogenating an aqueous solution of 3-hydroxypropanal using an oxide-supported metal hydrogenation catalyst in a first, low temperature, stage and continuing hydrogenation in a second, high temperature, stage using an activated carbon-supported metal hydrogenation catalyst.

Hydrogenation processes may be characterized by the conversions, selectivities, and space-time yields achievable therewith. Percent conversion of 3-hydroxypropanal is defined by:

$$X = \% \text{ Conversion of } HPA = \frac{\text{moles of } HPA \text{ converted}}{\text{moles of } HPA \text{ supplied}} \times 100$$

Selectivity of the hydrogenation process is a measure of the amount of converted 3-hydroxypropanal which is converted into the desired product:

$$\% \text{ Selectivity} = \frac{\text{moles of } 1, 3\text{-propanediol}}{\text{moles of } HPA \text{ converted}} \times 100$$

The space-time yield is another important characteristic for continuous hydrogenation processes, stating the achievable quantity of product per unit time and reaction volume.

When hydrogenating 3-hydroxypropanal to 1,3-propanediol on a large industrial scale, it is vital, with regard to the economic viability of the hydrogenation process and the quality of the product, for conversion and selectivity to be as close as possible to 100%. The 1,3-propanediol may be separated from the water as well as remaining 3-hydroxypropanal and secondary products contained in the product stream by distillation after the hydrogenation. However, this distillative separation is rendered very difficult by residual 3-hydroxypropanal and secondary products and may even become impossible due to reactions between the residual 3-hydroxypropanal and 1,3-propanediol to yield acetals such as 2-(2'-hydroxyethyl)-1,3-dioxane (HED), which have a boiling point close to the boiling point of 1,3-propanediol. Thus, the lower the conversion and selectivity, the poorer the achievable product quality.

In order to produce 1,3-propanediol economically, it is also important for the catalyst to exhibit high activity for the hydrogenation of 3-hydroxypropanal. The objective should thus be to find a process in which the smallest possible quantity of catalyst is necessary for the production of 1,3-propanediol; i.e., it is desirable to achieve the greatest possible conversion of 3-hydroxypropanal to 1,3-propanediol with a small volume of catalyst.

Another important quality criterion for hydrogenation catalysts is their operational service life. Good catalysts should ensure high conversion and selectivity in the hydrogenation of 3-hydroxypropanal to 1,3-propanediol over the course of their service life.

It is an object of the present invention to provide an improved process for the preparation of 1,3-propanediol via the hydrogenation of 3-hydroxypropanal whereby the service life of the hydrogenation catalyst is extended.

SUMMARY OF THE INVENTION

The present invention provides an improved process for the hydrogenation of 3-hydroxypropanal to 1,3-propanediol which comprises purifying an aqueous solution of 3-hydroxypropanal by contacting said aqueous solution with a purifying agent prior to hydrogenation.

The present invention further provides a process for the preparation of 1,3-propanediol which comprises: a) contacting an aqueous solution of 3-hydroxypropanal with a purifying agent; and b) hydrogenating said aqueous solution of 3-hydroxypropanal to 1,3-propanediol.

DETAILED DESCRIPTION OF THE INVENTION

The process of the current invention comprises an improved process for the hydrogenation of 3-hydroxypropanal (HPA). In the first stage, an aqueous HPA solution is contacted with a purifying agent; in the subsequent stage (or multiple stages), the contacted HPA solution is hydrogenated to 1,3-propanediol (PDO).

There are various hydrogenation processes known for the conversion of HPA to PDO that utilize aqueous HPA feeds. The purification stage of the present invention is applicable to, and combinable with, all said processes. Most preferably, the purification stage of the present invention is applied to the hydrogenation processes disclosed in U.S. Pat. No. 5,334,778 and in copending patent application, Ser. No. 60/099,235.

It has been found that hydrogenation catalysts are deactivated more rapidly than desired in the preparation of PDO via the hydrogenation of HPA. The deactivation of the catalysts is believed to be due to the adverse interaction between impurities in the aqueous HPA feed and the hydrogenation catalysts employed.

It has been found that treatment of the aqueous HPA feed with a purifying agent prior to hydrogenation improves performance and lifetime of the hydrogenation catalysts. Surprisingly, the initial activity of the hydrogenation catalyst is particularly enhanced. Purifying agents useful in the process of the present invention comprise purifying carbons, purifying silica compositions, diatomaceous earths and zeolites.

The most preferred purifying agents useful in the process of the present invention comprise purifying carbons.

When the purifying agents employed in the process of the present invention are purifying carbons, the carbons are those typically employed as decolorizing carbons. Typically they are activated carbons commercially available from various vendors.

After the purifying agent contacting stage of the process is carried out, the hydrogenation may be carried out using the methods disclosed in U.S. Pat. No. 5,334,778, incorporated herein by reference. For example, stirred reactors or flow reactors can be used. A fixed-bed hydrogenation reactor is particularly suitable for conducting the hydrogenation on an industrial scale. In such a reactor, the liquid reaction mixture flows or trickles over the fixed-bed catalyst together with the hydrogen introduced. To ensure good distribution of the hydrogen in the reaction mixture and uniform distribution of the gas/liquid mixture over the entire cross-section of the fixed bed, the liquid reaction mixture and hydrogen can be passed together through static mixers before the catalyst bed. Trickle bed reactors are particularly preferred and are described in Kirk-Othmer Encyclopedia of Chemical Technology, Third Edition, Volume 19, pages 880–914 (especially page 884).

The 3-hydroxypropanal is generally fed to the reactor as an aqueous solution having a 3-hydroxypropanal concentration of between 2 and 20 wt %, preferably between 5 and 15 wt %, based on the weight of water and feed, and a pH between about 2.5 and 7.0, preferably between about 3.5 and 5.5. In continuous processes, liquid hourly space velocities between about 0.1 and 10 per hour are preferred. The hydrogenation reaction is conducted at a hydrogen pressure of about 5 to 300 bar, preferably at a hydrogen pressure of less than about 90 bar, more preferably from about 10 bars to 60 bars.

EXAMPLES

Examples 1–5 and Comparative Examples A–B

These examples demonstrate the greater conversion and longer catalyst lifetime resulting from the pretreatment of aqueous HPA feed with activated carbon. Comparative examples employ the same catalyst and process conditions, but lack the carbon pretreatment.

The catalysts were tested under steady-state conditions in order to ascertain long-term performance. Hydrogenation was performed continuously in a trickle bed apparatus (Kirk-Othmer Encyclopedia of Chemical Technology, Third Edition, Volume 19, pages 880–914 (especially page 884)) having a reactor volume of 140 ml. The hydrogenation apparatus consisted of a liquid vessel, the fixed bed reactor, and a liquid separator. For examples employing treatment of the aqueous feed stream with activated carbon (i.e., the process of the present invention), the activated carbon bed was placed in series directly before (upstream of) the fixed bed reactor, but before admixture with hydrogen. The activated carbon bed was maintained in a tube with an inner diameter of 10 mm and was fed with the aqueous 3-hydroxypropanal feed from the bottom. The activated carbon bed had a volume of 20 ml. The carbon treatment bed/tube was kept under ambient temperature and pressure.

For Comparative examples, the entire tube assembly was removed.

The hydrogenation reaction temperature was adjusted by means of a heat transfer medium/oil circuit. The pressure and hydrogen stream were electronically controlled. The activated carbon-treated aqueous 3-hydroxypropanal solution (or non carbon-treated stream, for the comparative examples) was apportioned to the hydrogen stream with a pump and the mixture introduced into the top of the fixed bed reactor (trickle bed operation).

Once the mixture had passed through the reactor, the resultant product was removed from the separator at regular intervals. In every case, 30 ml of catalyst was used and the 3-hydroxypropanal concentration in the feed solution was 10 wt. %, with a pH of about 4.0. The hydrogenation temperature was 40° C., the hydrogen pressure 40 bar, and the liquid hourly space velocity, LHSV, was 1.0 per hour. Table 1 summarizes the results of the tests according to various examples. The residual 3-hydroxypropanal concentration in the reaction product was measured by GC and used in calculating the reported conversions. In all examples, the selectivity was greater than 98% (1,3-propanediol concentration measured by gas chromatography).

The hydrogenation catalysts employed in the examples (and comparative examples) were:

| | Catalyst |
|---|---|
| 1 | Degussa H 3036 (5% Ru/silica) |
| 2 | Degussa H 3051 (5% Ru/silica) |
| 3 | 2% Ru/TiO$_2$ |

Catalysts identified as "Degussa" were obtained from Degussa AG, Frankfurt, Germany. The TiO$_2$ supported catalyst was prepared according to the following method:

1. The water absorption of the support was determined in g of H$_2$O per 100 g of support.
2. RuCl3 was dissolved in distilled water for loading 250 ml of support (see Table 1).
3. 250 ml of support were introduced into a coating pan and the RuCl$_3$ solution was poured over the support while the pan was rotating.
4. The coated support was dried for 16 hours in air at room temperature and then heated to 200° C. in air in a tube furnace.

5. The catalyst was then reduced with hydrogen at 200° C. for 8 hours followed by cooling in hydrogen until the catalyst reached room temperature.
6. The reduced catalyst was washed until free of chloride with three 40 ml portions of distilled water.

The activated carbon samples utilized in the examples were commercially available materials. They are representative of the many commercial carbons available.

Carbon:
  Norit ROX 0,8, Norit Nederland B.V., P.O. Box 105, 3800 AC Amersfoot, The Netherlands, obtained from Norit Adsorption GmbH, Dusseldorf, Germany.
  Filtrasorb F400, obtained from Chemviron Carbon, Boulevard de la Wolwe 60 bte 1, 1200 Brussels, Belgium.
  CarboTech Activated Carbon AG 1–3, obtained from CarboTech Aktivkohlen Gmbh, Franz Fischer Weg 61, D-45307 Essen, Germany.

Table 1 shows the results of hydrogenation runs with and without carbon pretreatment with various catalysts. Differences in operating times between the carbon bed and the catalyst are due to the fact that one carbon bed was used (and remained in place) for a number of catalyst tests.

Comparative Example A, Example 1 and Example 2 employed the same catalyst (catalyst 1), no carbon in comparative Example A, two different carbons in Examples 1 and 2. In each case, at each catalyst operating time, HPA conversions were higher in Examples 1 and 2 than in Comparative Example A. Moreover, catalyst deactivation, as indicated by a decrease in percent conversion with time, was slowed in Examples 1 and 2 versus comparative Example A.

Examples 3 and 4, for which there is no comparative run, used catalyst 2. They show slow rates of deactivation versus run time. Example 4 shows an exceptionally high conversion from the combination of catalyst 2 and the CarboTech AG 1–3 carbon.

Comparative Example B and Example 5 utilize catalyst 3. The rate of in HPA conversion is much reduced in the presence of the carbon pretreatment.

TABLE 1

Effect of carbon treatment on catalyst life and activity

| Example | Catalyst | Carbon | Carbon Bed Operating Time (hrs) | Catalyst Operating time (hrs) | HPA Conversion percent |
|---|---|---|---|---|---|
| A (comp) | 1 | NONE | — | 18 | 69 |
| | | | — | 42 | 65 |
| | | | — | 90 | 55 |
| 1 | 1 | Norit ROX 0.8 | 20 | 18 | 88 |
| | | | 44 | 42 | 84 |
| | | | 117 | 90 | 79 |
| 2 | 1 | Filtrasorb F400 | 17 | 17 | 76 |
| | | | 41 | 41 | 73 |
| | | | 65 | 65 | 71 |
| 3 | 2 | Filtrasorb F400 | 123 | 25 | 73 |
| | | | 147 | 49 | 70 |
| 4 | 2 | Carbo Tech AG 1–3 | 29 | 14 | 96 |
| | | | 48 | 33 | 90 |
| B (comp) | 3 | NONE | — | 16 | 89 |
| | | | — | 93 | 68 |
| 5 | 3 | Filtrasorb F400 | 598 | 10 | 93 |
| | | | 636 | 48 | 92 |

What is claimed is:

1. A process for the preparation of 1,3-propanediol which comprises sequentially: a) providing an aqueous solution of 3-hydroxypropanal; b) purifying the aqueous solution of 3-hydroxypropanal by contacting the aqueous solution of 3-hydroxypropanal with purifying agent; and c) downstream of the purifying, hydrogenating the 3-hydroxypropanal of the purified aqueous solution of 3-hydroxypropanal to 1,3-propanediol, wherein the purifying agent is selected from the group consisting of purifying carbons, purifying silica compositions, diatomaceous earths and zeolites.

2. The process of claim 1 wherein the purifying agent is selected from the group consisting of purifying carbons.

3. The process of claim 1 wherein the hydrogenating converts at least 70% of the 3-hydroxypropanal to 1,3-propanediol.

4. The process of claim 1 wherein the hydrogenation catalyst comprises ruthenium.

5. The process of claim 1, wherein the hydrogenation is carried out in at least one fixed-bed hydrogenation reactor, the temperature in the bed being in the range of 30° C. to 180° C.

6. The process of claim 1 wherein the purification stage and hydrogenation stages are carried out in separate fixed bed reactors.

7. The process of claim 1 wherein the purifying agent is activated carbon.

8. The process of claim 1 wherein the purifying agent is selected from the group consisting of purifying silica compositions.

9. The process of claim 1 wherein the purifying agent is selected from the group consisting of diatomaceous earths.

10. The process of claim 1 wherein the purifying agent is selected from the group consisting of zeolites.

11. A process for the preparation of 1,3-propanediol which comprises sequentially: a) hydrating acrolein in aqueous phase in the presence of an acidic catalyst to form to form an aqueous solution of 3-hydroxypropanal; b) purifying the aqueous solution of 3-hydroxypropanal by contacting the aqueous solution of 3-hydroxypropanal with purifying agent; and c) downstream of the purifying, hydrogenating the 3-hydroxypropanal to 1,3-propanediol, wherein the purifying agent is selected from the group consisting of purifying carbons, purifying silica compositions, diatomaceous earths and zeolites.

12. The process of claim 11 wherein the purifying agent is a purifying carbon.

13. The process of claim 11 wherein the purifying agent is activated carbon.

14. The process of claim 11 wherein the purifying agent is selected from the group consisting of purifying silica compositions.

15. The process of claim 11 wherein the purifying agent is selected from the group consisting of diatomaceous earths.

16. The process of claim 11 wherein the purifying agent is selected from the group consisting of zeolites.

* * * * *